United States Patent [19]

Scheeren et al.

[11] Patent Number: 5,079,349
[45] Date of Patent: Jan. 7, 1992

[54] TRIMETHYLSILYL ACETYLENE COMPOUNDS, THEIR PREPARATION AND THEIR USE IN THE PREPARATION OF DAUNOMYCINONE DERIVATIVES

[75] Inventors: Johan W. Scheeren, Malden; Joannes F. M. De Bie, Nijmegen; Dirk De Vos, Oegstgeest, all of Netherlands

[73] Assignee: Pharmachemie B.V., Haarlem, Netherlands

[21] Appl. No.: 473,537

[22] Filed: Feb. 1, 1990

[30] Foreign Application Priority Data

Feb. 10, 1989 [NL] Netherlands .......................... 8900328

[51] Int. Cl.$^5$ ............................................. C07H 15/24
[52] U.S. Cl. ...................................... 536/6.4; 552/201
[58] Field of Search ................ 536/6.4, 50; 552/201

[56] References Cited

PUBLICATIONS

Suzuki et al "A Novel Synthesis of the α-Hydroxyketone Moiety of Anthracyclinones by the Use of 2--Trimethylsilylethynylcerium (III) Reagents" Chemistry Letters, pp. 1543-1546, 1984.
Kelley et al "An Efficient, Regiospecific Synthesis of (±)Daunomycinone" Tetrahedron, vol. 40, No. 22, pp. 4569-4577, 1984.
Gupta et al "An Efficient Enantiocontrolled Synthesis of (±-4-Demethoxydaunomycinone" Tetrahedron, vol. 40, No. 22, pp. 4657-4667, 1984.
Angelo et al "Utilisation D'Alkoxyacetates Chiraux--Equivalents De L'Hydroxyacetaldehyde—En Aldolisation Stereocontrolee" Tet. Letters 24(52) 5869, 1983.

Krohn et al "Totalsynthese des Daunomycinons" Chem. Ber. 112, 3453-3471 (1979).

*Primary Examiner*—Nathan M. Nutter
*Attorney, Agent, or Firm*—Browdy and Neimark

[57] ABSTRACT

The invention relates to novel compounds of the formulae

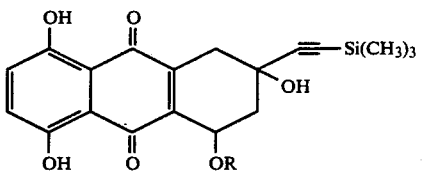

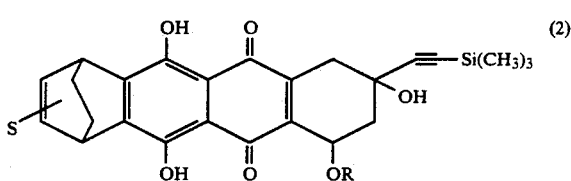

wherein S is H, alkyl or alkoxy and R is a good leaving group, and to the preparation of these compounds in a stereospecific manner to obtain a configuration wherein OH at C-3 and OR at C-1 are in the cis-position, which compounds can be used for the synthesis of daunomycinone and derivatives thereof.

Daunomycinone can be used for the preparation of daunomycin and adriamycin.

10 Claims, No Drawings

TRIMETHYLSILYL ACETYLENE COMPOUNDS, THEIR PREPARATION AND THEIR USE IN THE PREPARATION OF DAUNOMYCINONE DERIVATIVES

This invention relates to trimethylsilyl ethynyl compounds, their preparation and their use in the preparation of daunomycinone derivatives.

Daunomycinone is a compound of the formula

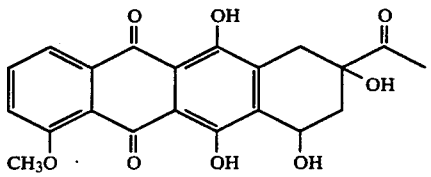

Derivatives thereof include daunomycin (which has an antibiotic and antineoplastic activity) and adriamycin or doxorubicin (which also has an antibiotic and antineoplastic activity).

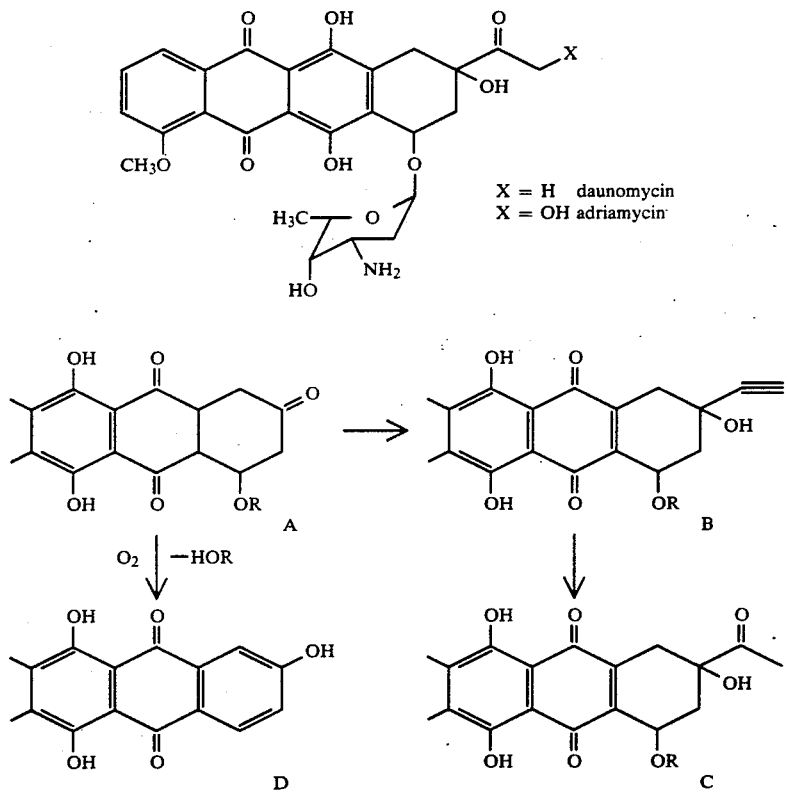

X = H daunomycin
X = OH adriamycin

An important step in a number of syntheses of daunomycinone and derivatives is the conversion of a ketone group to a α-hydroxy, acetyl group as described for the conversion of A to C.

Such syntheses are described in an article by T. R. Kelly et al, Tetrahedron, Vol. 40, No. 22, 4569-4577 (1984) and in an article by K. Krohn and K. Tolkiehn, Chem. Ber. 112, 3453-3471 (1979).

A problem in the above conversion of a ketone group to a OH, acetyl group is the removal of the group OR under alkaline conditions and oxidation in air, whereby the aromatic compound D is produced, which compound is an undesired by-product.

The methods described in the above literature for obtaining the α-hydroxy-acetyl function have several further disadvantages. These methods are not suitable for the synthesis of daunomycinone derivatives on a gram scale or on a larger scale. When using ethynyl magnesium bromide a 30-40 fold excess is required to obtain a yield of maximum 50% (K. Krohn and K. Tolkiehn, Tetrahedron Letters, 4023-4026 (1978)).

Moreover the applicant has found that when enlarging the scale the yield decreases due to increasing elimination of ROH, which leads to an increased amount of the undesired by-product D.

By using lithium acetylide [R. P. Potman, Thesis Catholic University Nijmegen, Chapter 5, 79-94 (1985)] the number of equivalents of acetylide can be reduced to 5. The yield on a small scale (50-100 mg) can be increased to max. 50%; also in this case enlarging the scale resulted in a decrease in the yield and increasing production of D. However, also in the latter case the product, wherein the OH group and the OR group are in the trans-position, is formed, however in a relatively small amount.

M. Suzuki et al, Chemistry Letters, 1543-1546 (1984) discloses the conversion of a ketone function by means of Li—C≡C—Si(CH$_3$)$_3$/CeCl$_3$:

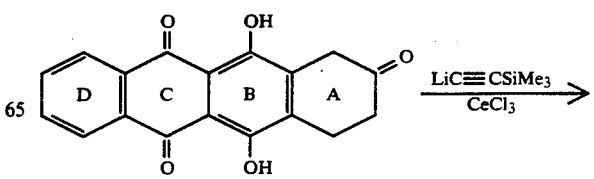

-continued

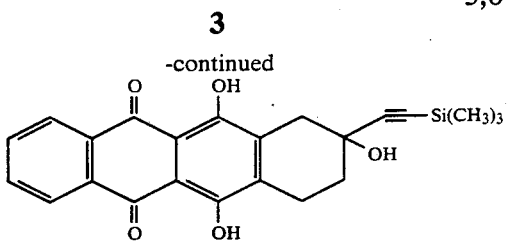

In this reaction, in which ring A does not have a OH function, the presence of CeCl$_3$ has appeared to be essential.

It has been found that by means of lithium-trimethylsilyl acetylene without using CeCl$_3$ a ketone compound of the present type can be stereospecifically converted to a cis α-hydroxytrimethylsilyl acetylene compound in a yield of 50–80%. The trans-isomer was not detected. This synthesis results in a racemic mixture; in practice resolution is carried out in a later stage of the total synthesis: the daunomycinone obtained is reacted with a chiral sugar (i.e. one enantiomer) and the obtained diastereomers are seperated.

Scale enlargement to about 10 grams does not result in a reduction of the yield.

The present novel compounds which can be used in total syntheses which are known per se, are:

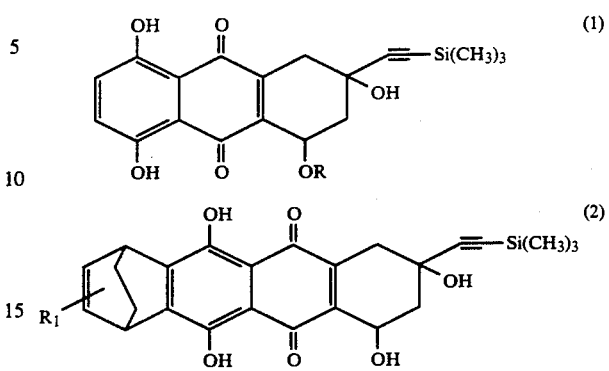

wherein R$_1$ is H, alkyl or alkoxy and R is a removable protecting group. Preferably R is removed with the aid of an acid.

By analogy with the above syntheses of Kelly et al. and Tolkiehn et al one can operate according to the following schemes which are given only by way of example:

scheme 1:

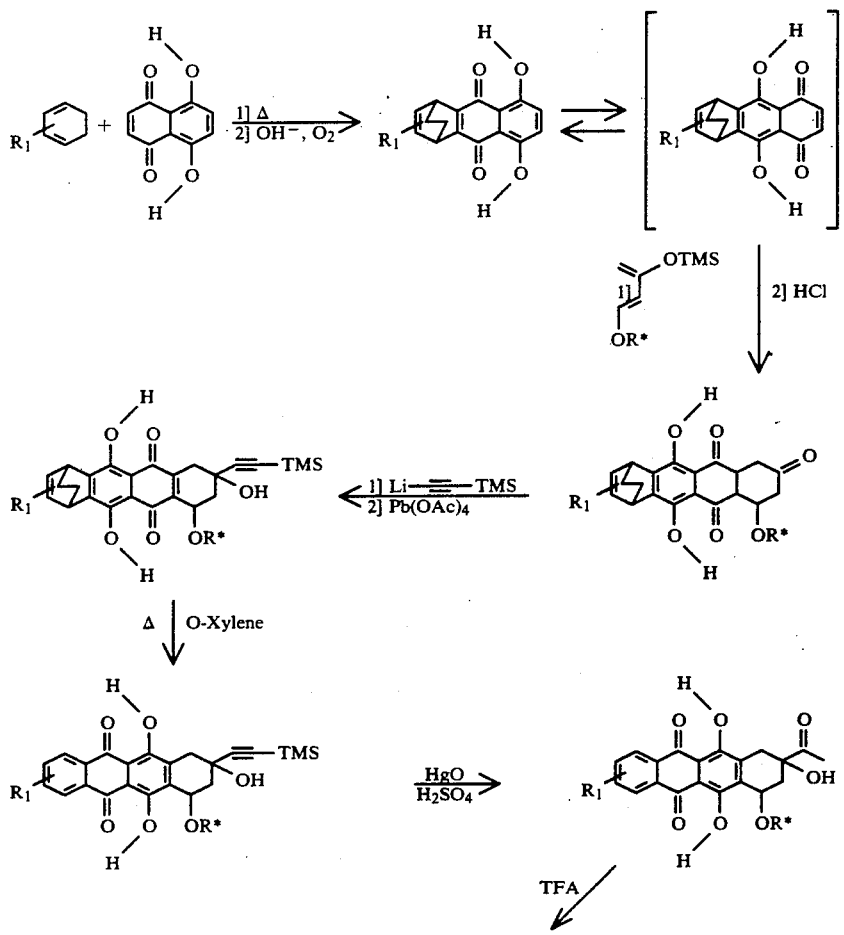

scheme 1:
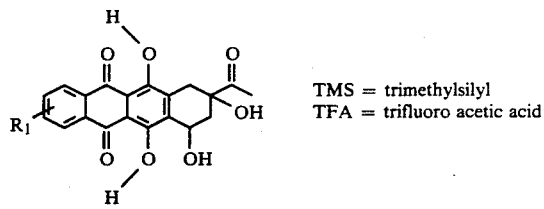
-continued
TMS = trimethylsilyl
TFA = trifluoro acetic acid
Scheme 2:
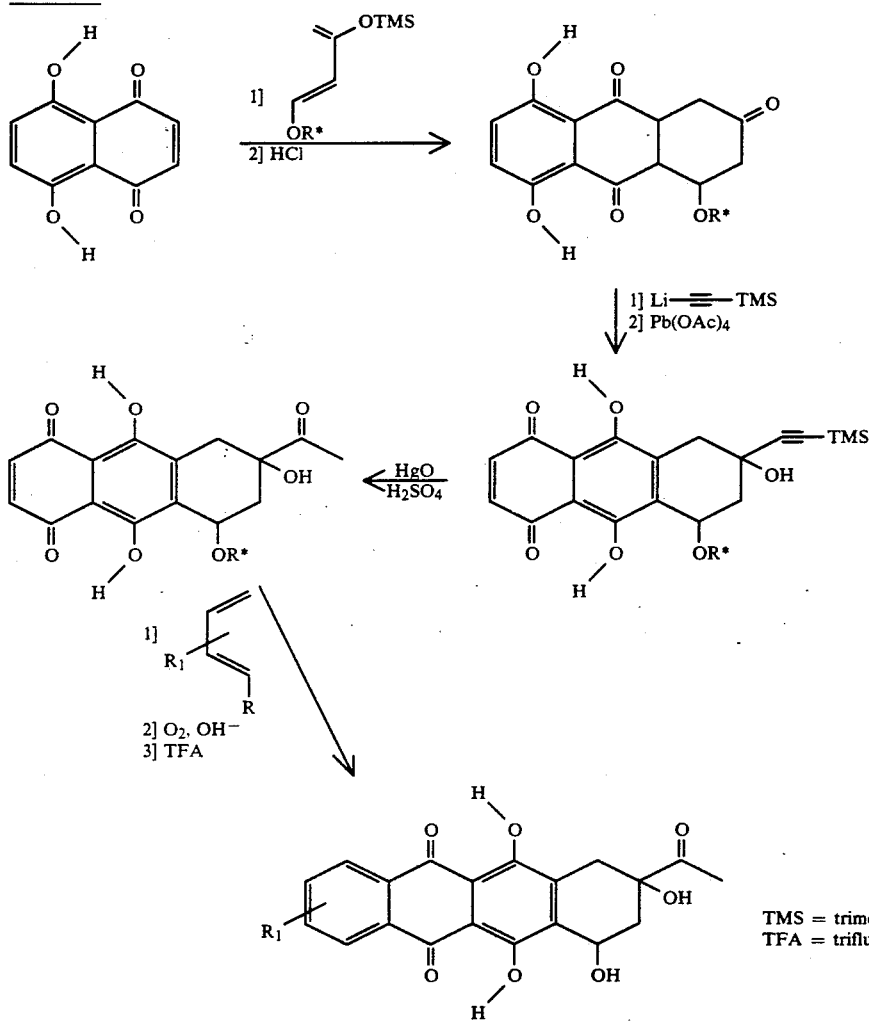
TMS = trimethylsilyl
TFA = trifluoro acetic acid
The invention is further illustrated by the following examples.
EXAMPLE 1
1,4,9,10-tetrahydro-5,8-dihydro-9,10-dioxo-1,4-ethanoanthracene (I)
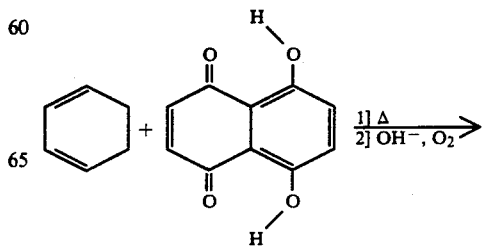

-continued

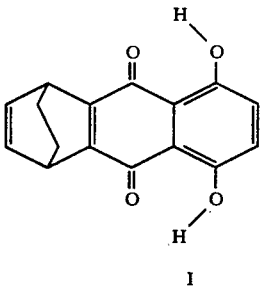

I 19.0 g (100 mmol) of pure naphtazarin and 12.5 g (160 mmol) of 1,3-cyclohexadiene were refluxed in 190 ml of THF for 5 days. The reaction was followed by means of TLC (ethylacetate:n-hexane, 2:5). The colour of the solution changed from red to yellow/brown. After evaporating the product was purified by stirring the residue in 200 ml of petroleum ether 40/60 for one hour. The solid was filtered off. Yield: 23.8 g (88%).

The yellow compound was added to a solution of 20.0 g of NaOH in 750 ml of water while stirring. The solution was stirred for one hour while compressed air was passed through. The reaction was followed by means of TLC (ethylacetate:n-hexane, 2:5). After the reaction 35 ml of concentrated HCl (37%) was added. The precipitated solid compound was filtered off. This red compound was rinsed from the filter with chloroform, whereafter the organic phase was washed with saturated sodium bicarbonate solution. After drying over anhydrous sodium sulphate and evaporating 20.1 g (85% overall 75%) of the compound I could be isolated. Melting point 203°-204° C.

$^1$H-NMR (90 MHz, CDCl$_3$, TMS internal standard): $\delta$=1.16-1.58 ppm (4H, m, CH$_2$—CH$_2$), $\delta$=4.49 ppm (2H, m, H$_1$ and H$_4$), $\delta$=6.35 ppm (2H, dd, H—C=C—H), $\delta$=7.03 ppm (2H, s, ArH), $\delta$=12.48 ppm (2H, s, ArOH).

1,4,6a,9,10,10a-hexahydro-5,12-dihydroxy-7-tert-butoxy-1,4-ethanonaphtacene-6,9,11-(10H)-trione (II)

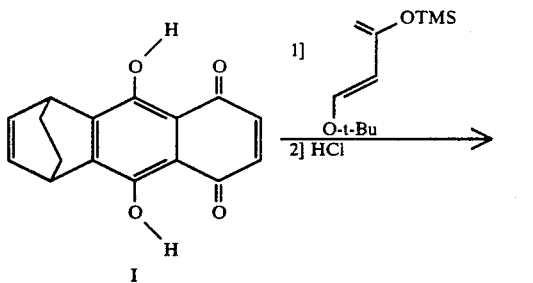

I

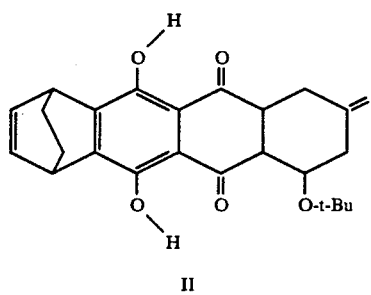

II 19.4 g (72 mmol) of (I) was dissolved in 300 ml of toluene and placed under an argon atmosphere. 23.2 g (108 mmol, 1.5 e.q.) of 1-tert-butoxy-3-trimethylsilyloxy butadiene was added thereto. The course of the reaction was followed by means of TLC (ethylacetate:n-hexane, 2:5). After stirring at room temperature for 5 days the reaction mixture was evaporated and taken up in 190 ml of cold THF (0° C.). 9.7 ml 1M HCl solution was added thereto and the solution was stirred at 0° C. for 15 minutes. The course of the reaction was followed by means of TLC. (ethylacetate:n-hexane, 2:5). Thereafter 500 ml of water was added and the aqueous layer was extracted with methylene chloride (2×500 ml). The organic layer was dried over anhydrous sodium sulphate and evaporated.

The product was purified by stirring the residue in 200 ml of diethylether for one night. The solid (pale yellow) was filtered off. The filtrate was evaporated and further purified by means of flash column chromatography (column 25 cm, 5 cm O$\emptyset$, eluent ethylacetate:n-hexane, 2:3). The total yield was 22.2 g (75%). Melting point 154°-158° C.

$^1$H-NMR (90 MHz, CDCl$_3$, TMS internal standard): (Mixture of endo and exo isomers) $\delta$=0.7 ppm (9H, s, C(CH$_3$)$_3$), $\delta$=1.2-1.61 ppm (4H, m, CH$_2$—CH$_2$), $\delta$=2.1-2.57 ppm (3H, H$_{10}$(ax)+H$_8$(eq)+H$_8$(ax)), $\delta$=3.23-3.6 ppm (3H, H$_{10a}$+H$_{6a}$+H$_{10}$(eq)), $\delta$=4.39 ppm (1H, m, H$_7$), $\delta$=4.47-4.63 ppm (2H, m, H$_1$+H$_4$), $\delta$=6.45 ppm (2H, dd, H—C=C—H), $\delta$=11.83 ppm (1H, s, ArOH), $\delta$=12.30 ppm (1H, s, ArOH).

Cis-9-trimethylsilylethynyl-1,4,7,8,9,10-hexahydro-6,9,11-trihydroxy-7-tert-butoxy-1,4-ethanonaphtacene-5,12-dione (III)

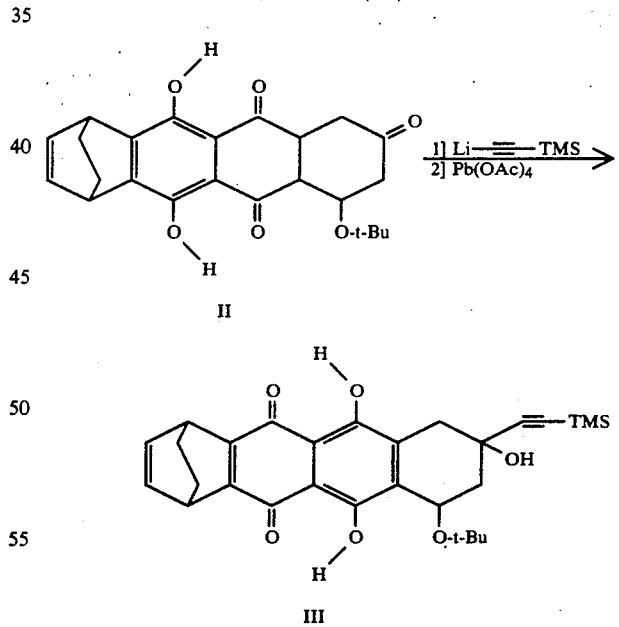

III 4.2 g (0.043 mol) of trimethylsilyl acetylene* was dissolved in 450 ml THF, which had been distilled over sodium, and thereafter an argon atmosphere was applied. The solution was cooled to −78° C. and 26.2 ml (0.042 mol) of 1.6M n-butyllithium was added. After stirring at −78° C. for half an hour 3.45 g (0.084 mol) of II** was added. The reaction mixture was stirred at −78° C. for 3 hours while the reaction was being followed by means of TLC (ethyl acetate:n-hexane, 2:5).

At the end of the reaction the reaction mixture was permitted to warm up slowly to room temperature and 150 ml of a 10% ammonium chloride solution was added. After 15 minutes 300 ml of water was added and the solution was twice extracted with 300 ml of chloroform. The combined organic fractions were dried over anhydrous sodium sulfate and evaporated after filtration. The residue was dissolved in 60 ml of glacial acetic acid and 3.7 g (0.0084 mol) of lead tetraacetate was added to the solution. After stirring for one night 200 ml of water was added. The red solid which precipitated, was removed by filtration and washed from the filter. The solution was extracted with 75 ml of a saturated sodium bicarbonate solution. The organic phase was dried over anhydrous sodium sulfate, filtered and evaporated. The product was purified by means of a column separation (column 15 cm ∅5 cm, eluent ethylacetate:n-hexane, 1:4). The yield of III was 3.2 g (75%).

* The amount of triethylsilyl acetylene should always be in excess of the amount of n-butyl lithium. Otherwise the starting materialen will aromatize.
** The compounds II, VII, IX and XI should be thoroughly dried over $P_2O_5$ and under vacuum prior to the reaction.

$^1$H-NMR (90 MHz, CDCl$_3$, TMS internal standard): (Mixture of endo and exo isomers) $\delta = 0.27$ ppm (9H, s, Si(CH$_3$)$_3$), $\delta = 1.40$ ppm (9H, s, C(CH$_3$)$_3$), $\delta = 1.20-1.80$ ppm (4H, m, CH$_2$—CH$_2$), $\delta = 1.94$ ppm (1H, dd, J=14.5 Hz and J=3 Hz, H$_8$(ax)), $\delta = 2.67$ ppm (1H, d, J=14.5 Hz, H$_8$(eq)), $\delta = 3.04$ ppm (1H, d, J=17.5 Hz, H$_{10}$(ax)), $\delta = 3.55$ ppm (1H, d, J=17.5 Hz, H$_{10}$(eq)), $\delta = 4.63$ ppm (2H, m, H$_1$+H$_4$), $\delta = 5.27$ ppm (1H, m, H$_7$), $\delta = 5.72$ ppm (1H, s, OH), $\delta = 6.48$ ppm (2H, dd, H—C≡C—H), $\delta = 12.95$ ppm (1H, s, ArOH), $\delta = 13.12$ ppm (1H, s, ArOH).

Cis-9-trimethylsilylethynyl-7,8,9,10-tetrahydro-6,9,11-trihydroxy-7-tert-butoxy-naphthacene-5,12-dione (IV)

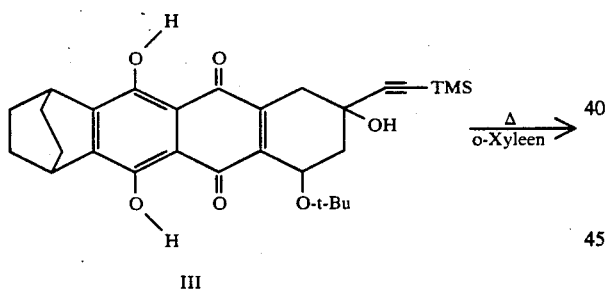

III

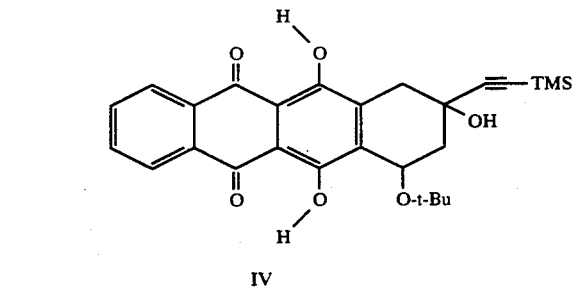

IV 2.9 g (5.7 mmol) of (III) was dissolved in 30 ml of o-xylene. The solution was refluxed at 150° C. for 5 hours. The solution was evaporated and taken up in 30 ml of ether. The ether was refluxed for half an hour. After cooling the solution to room temperature, the orange solid was filtered off. The yield was 2.5 g (91%). Melting 214°-216° C.

$^1$H-NMR (90 MHz, CDCl$_3$, TMS internal standard): $\delta = 0.18$ ppm (9H, s, Si(CH$_3$)$_3$), $\delta = 1.40$ ppm (9H, s, C(CH$_3$)$_3$), $\delta = 1.99$ ppm (1H, dd, J=14.5 Hz and J=3 Hz, H$_8$(ax)), $\delta = 2.76$ ppm (1H, d, J=14.5 Hz, H$_8$(eq)), $\delta = 3.02$ ppm (1H, d, J=19.5 Hz, H$_{10}$(ax)), $\delta = 3.67$ ppm (1H, d, J=19.5 Hz, H$_{10}$(eq)), $\delta = 5.33$ ppm (1H, m, H$_7$), $\delta = 5.87$ ppm (1H, s, OH), $\delta = 7.72-7.87$ ppm (2H, m, ArH), $\delta = 8.25-8.39$ ppm (2H, m, ArH), $\delta = 13.33$ ppm (1H, s, ArOH), $\delta = 13.67$ ppm (1H, s, ArOH).

Cis-9-acetyl-7,8,9,10-tetrahydro-6,9,11-trihydroxy-7-tert-butoxy-naphthacene-5,12-dione (V)

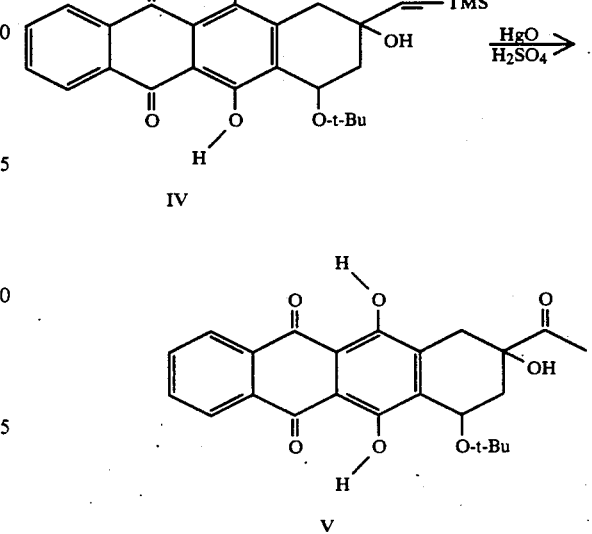

IV

V 2.5 g (5.2 mmol) of (IV) was dissolved in 110 ml of THF. To this solution 55 ml of 3M sulphuric acid and 1.2 g (5.2 mmol) mercury (II) oxide was added. The solution was stirred at room temperature for 24 hours. Thereafter the reaction mixture was poured into 270 ml of 1M HCl and extracted with chloroform (3×200 ml). The organic phase was dried over anhydrous sodium sulphate, filtered off and evaporated. The product was purified by means of column chromatography (column 15 cm, 5 cm ∅, eluent ethylacetate:n-hexane, 2:5). Yield: 1.6 g (72%). Melting point 217°-220° C.

$^1$H-NMR (90 MHz, CDCl$_3$, TMS internal standard): $\delta = 1.42$ ppm (9H, s, C(CH$_3$)$_3$), $\delta = 1.90$ ppm (1H, dd, J=14.5 Hz and J=3 Hz, H$_8$(ax)), $\delta = 2.38$ ppm (1H, d, J=14.5 Hz, H$_8$(eq)), $\delta = 2.43$ ppm (3H, s, CH$_3$), $\delta = 3.04$ ppm (1H, d, J=20 Hz, H$_{10}$(ax)), $\delta = 3.32$ ppm (1H, d, J=20 Hz, H$_{10}$(eq)), $\delta = 5.43$ ppm (1H, m, H$_7$), $\delta = 5.96$ ppm (1H, s, OH), $\delta = 7.76-7.89$ ppm (2H, m, ArH), $\delta = 8.28-8.44$ ppm (2H, m, ArH), $\delta = 13.37$ ppm (1H, s, ArOH), $\delta = 13.72$ ppm (1H, s, ArOH).

(±)-4-demethoxy-daunomycinone (9)

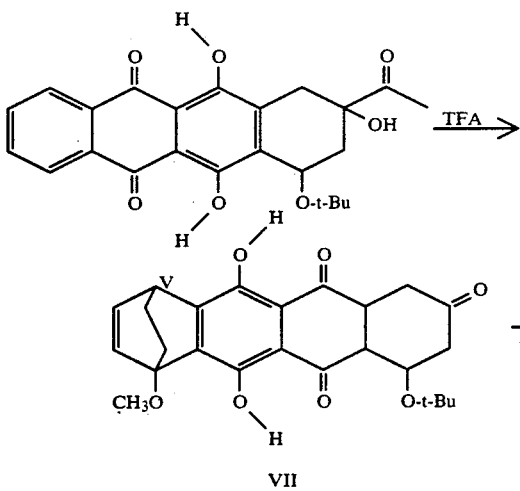

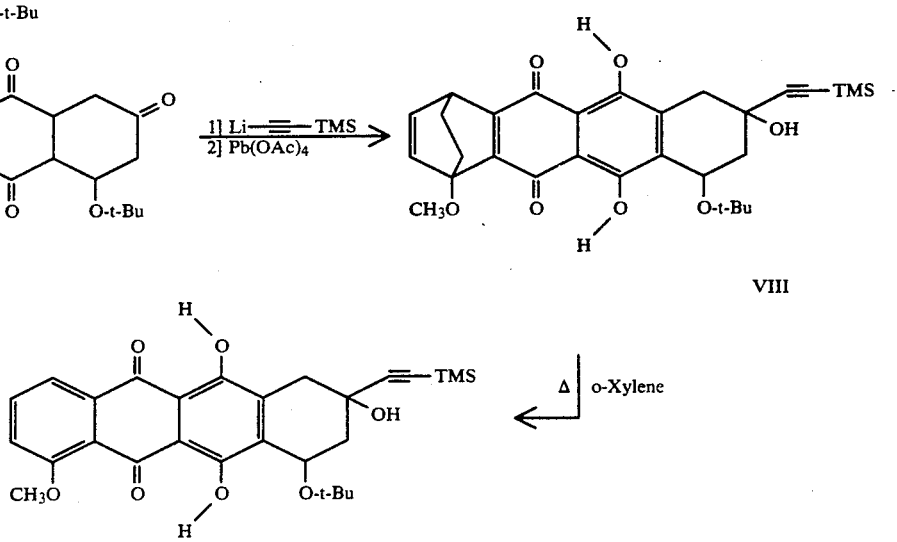

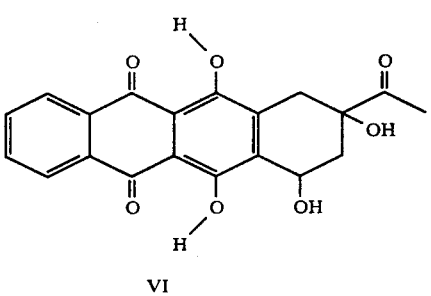

1.6 g (3.8 mmol) of (V) was dissolved in 20 ml of trifluoro acetic acid. The course of the reaction was followed by means of TLC (ethylacetate:n-hexane, 3:5). After about 10 minutes the starting material had been reacted and the solution was evaporated. For the subsequent coupling reaction with sugar the 4-demethoxy daunomycinone was recrystallized in CHCl$_3$/diethyl ether (16/28 ml). Yield (orange coloured product): 1.1 g (79%) melting point 182°–184° C.

$^1$H-NMR (90 MHz, CDCl$_3$, TMS internal standard):
δ=2.16 ppm (1H, d, J=14.5 Hz and J=5 Hz, H$_8$(ax)),
δ=2.38 ppm (1H, d, J=14.5 Hz, H$_8$(eq)), δ=2.43 ppm (3H, s, CH$_3$), δ=2.93 ppm (1H, d, J=18.5 Hz, H$_{10}$(ax)),
δ=3.24 ppm (1H, d, J=18.5 Hz, H$_{10}$(eq)), δ=3.80 ppm (1H, d, J=5 Hz, OH$_7$), δ=4.54 ppm (1H, s, OH$_9$),
δ=5.32 ppm (1H, br, s, H$_7$), δ=7.76–7.90 ppm (2H, m, ArH), δ=8.25–8.41 ppm (2H, m, ArH), δ=13.29 ppm (1H, s, ArOH), δ=13.56 ppm (1H, s, ArOH).

It was shown that in compound IV the C-9 OH group and the C-7 alkoxy group in ring A are in the cis-position with respect to each other: The difference between the cis and trans compounds appears from the $^1$H-NMR spectrum: the cis-compound has a smaller coupling constant between H$_7$ and H$_8$ (ax) [R. P. Potman et al, J.O.C., 49, 3628 (1984) and literature cited therein]. Furthermore the shift-difference between the geminal H$_{10}$ protons for the cis-compounds exceeds that for the trans-compound.

EXAMPLE 2

5.7 g (0.058 mol) of trimethylsilyl acetylene* was dissolved in 750 ml of THF, which had been distilled over sodium, and thereafter an argon atmosphere was applied. Then the solution was cooled to −78° C., and 37.9 ml 1.5M BuLi (0.057 mol) was added dropwise. The reaction mixture was stirred at −78° C. for 30 minutes. To the reaction mixture 5.0 g (0.0114 mol) VII** was added. The course of the reaction was followed by means of TLC (ethyl acetate:n-hexane, 2:5). The colour of the solution changed from green to yellow. After about two hours the reaction mixture was allowed to warm up slowly to room temperature and 250 ml of a 10% NH$_4$Cl solution was added. After stirring for 15 minutes the solution was diluted with 500 ml of water and twice extracted with 500 ml of chloroform. The combined organic fractions were evaporated and the residue was dissolved in 100 ml of glacial acetic acid. To the solution 5.5 g (0.012 mol) of lead tetraacetate was added and the solution was stirred at room temperature for one night. The course of the reaction was followed by means of TLC (ethylacetate:n-hexane, 2:5). The colour of the solution changed from yello/red to red. After the reaction the reaction mixture was poured into 400 ml of water. The red solid was removed by filtration and the filtrate was dissolved in chloroform. The organic fraction was washed with a saturated solution of sodium bicarbonate and dried over anhydrous sodium sulfate. After concentrating and recrystallizing in n-hexane red crystals VIII were isolated (5.1 g, 83%).

* The amount of trimethylsilyl acetylene should always be in excess of the amount of n-butyl lithium. Otherwise the starting materialen will aromatize.
** The compounds II, VII, IX and XI should be thoroughly dried over P$_2$O$_5$ and under vacuum prior to the reaction.

The crude reaction mixture was dissolved in 50 ml of o-xylene. The solution was refluxed for 3 hours (temperature of the oil bath: 150° C.). For the heating treatment with o-xylene reference is made to scheme 1 of this specification. The course of the reaction was followed by means of TLC (ethylacetate:n-hexane, 3:5) and the colour of the solution changed from red to orange. After the reaction the solution was evaporated and the product was recrystallized from diethyl ether. The yield (orange-coloured crystals) was 4.2 g (74%, overall yield, calculated with respect to the carbonyl compound (VII)). Melting point: 247°–250° C.

$^1$H-NMR (90 MHz, CDCl$_3$, TMS internal standard): $\delta=0.23$ ppm (9H, s, Si(CH$_3$)$_3$), $\delta=1.39$ ppm (9H, s, C(CH$_3$)$_3$), $\delta=1.99$ ppm (1H, dd, J=15 Hz, J=3 Hz, H$_8$(ax)), $\delta=2.72$ ppm (1H, d, J=15 Hz, H$_8$(eq)), $\delta=2.98$ ppm (1H, d, J=20 Hz, H$_{10}$(ax)), $\delta=3.64$ ppm (1H, d, J=20 Hz, H$_{10}$(eq)), $\delta=4.05$ ppm (3H, s, OCH$_3$), $\delta=5.35$ ppm (1H, m, H$_7$), $\delta=5.87$ ppm (1H, s, OH), $\delta=7.23$–8.05 ppm (3H, m, ArH), $\delta=12.99$ ppm (1H, s, ArOH), $\delta=13.8$ ppm (1H, s, ArOH).

EXAMPLE 3

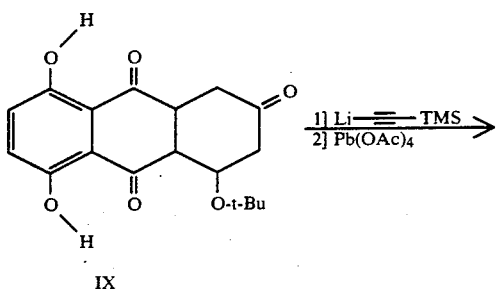

IX

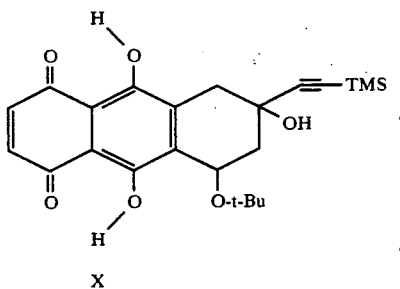

X 5.0 g (0.051 mol) trimethylsilyl acetylene* was dissolved in 600 ml of THF, which had been distilled over sodium, and thereafter an argon atmosphere was applied. The solution was cooled to −78° C. and 31.25 ml (0.050 mol) of 1.6M n-butyllithium was added. After stirring at −78° C. for half an hour 3.32 g (0.010 mol) of IX** was added. The reaction mixture was stirred at −78° C. for 2 hours while the reaction was followed by means of TLC (ethylacetate n-hexane 2:5). After the reaction the reaction mixture was permitted to warm up slowly to room temperature and 200 ml of a 10% ammonium chloride solution was added. After 15 minutes 400 ml of water was added and the solution was twice extracted with 400 ml of chloroform. The combined organic fractions were dried over anhydrous sodium sulfate and evaporated after filtration. The residue was dissolved in 75 ml of glacial acetic acid and 4.4 g (0.010 mol) lead tetraacetate was added to the solution. After stirring for one night 250 ml of water was added. The red solid which precipitated, was removed by filtration and washed from the filter with 400 ml of chloroform. The solution was extracted with 100 ml of a saturated sodium bicarbonate solution. The organic phase was dried over anhydrous sodium sulfate, filtrate and evaporated. The product was purified by means of a column separation (column 15 cm, ⌀5 cm, eluent ethyl acetate:n-hexane 1:4). The yield of X was 2.4 g (56%). Melting point 191°–193° C.

* The amount of trimethylsilyl acetylene should always be in excess of the amount of n-butyl lithium. Otherwise the starting materialen will aromatize.
** The compounds II, VII, IX and XI should be thoroughly dried over P$_2$O$_5$ and under vacuum prior to the reaction.

$^1$H-NMR (90 MHz, CDCl$_3$, TMS internal standard): $\delta=0.18$ ppm (9H, s, Si(CH$_3$)$_3$), $\delta=1.33$ ppm (9H, s, C(CH$_3$)$_3$), $\delta=1.87$ ppm (1H, dd, J=14.5 Hz, J=3.75 Hz, H$_2$(ax)), $\delta=2.64$ ppm (1H, d, J=14.5 Hz, H$_2$(eq)), $\delta=2.77$ ppm (1H, d, J=20 Hz, H$_4$(ax)), $\delta=3.47$ ppm (1H, d, J=20 Hz, H$_4$(eq)), $\delta=5.19$ ppm (1H, m, H$_1$), $\delta=5.57$ ppm (1H, s, OH), $\delta=7.18$ ppm (2H, s, ArH), $\delta=12.56$ ppm (1H, s, ArOH), $\delta=12.69$ ppm (1H, s, ArOH).

EXAMPLE 4

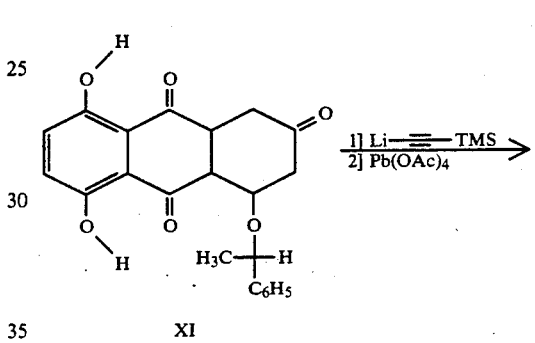

XI

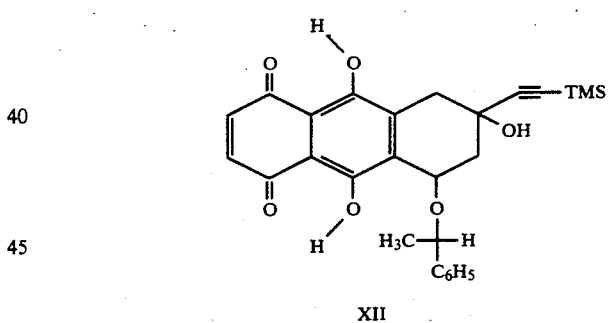

XII 1.3 g (0.0133 mol) trimethylsilyl acetylene* was dissolved in 150 ml of THF, which had been distilled over sodium, and thereafter an argon atmosphere was applied. The solution was cooled to −78° C. and 8.2 ml (0.013 mol) of 1.6M n-butyllithium was added. After stirring at −78° C. for half an hour 1.0 g (0.0026 mol) of XI** was added. The reaction mixture was stirred at −78° C. for 3 hours, while the reaction was followed by means of TLC (ethyl acetate:n-hexane, 2:5). After the reaction the reaction mixture was permitted to warm up slowly to room temperature and 50 ml of a 10% ammonium chloride solution was added. After 15 minutes 100 ml of water was added and the solution was twice extracted with 100 ml of chloroform. The combined organic fractions were dried over anhydrous sodium sulfate and evaporated after filtration. The residue was dissolved in 25 ml of glacial acetic acid and 1.15 g (0.0026 mol) of lead tetraacetate was added to the solution. After stirring for one night 75 ml of water was added. The red solid which precipitated, was removed by filtration and washed from the filter with 100 ml of chloroform. The solution was extracted with 25 ml of a saturated sodium bicarbonate solution. The organic phase was dried over anhydrous sodium sulfate, filtrated and evaporated. The product was purified by means of a column separation (column 15 cm, ∅3 cm, eluent ethyl acetate:n-hexane, 1:4). The yield of XII was 0.63 g (50%). Melting point: 163°-167° C.

\* The amount of trimethylsilyl acetylene should always be in excess of the amount of n-butyl lithium. Otherwise the starting materialen will aromatize.

\*\* The compounds II, VII, IX and XI should be thoroughly dried over $P_2O_5$ and under vacuum prior to the reaction.

400 MHz $^1$H-NMR (CDCl$_3$) mixture of diastereomers XIIa and XIIb $\delta = 12.67$ ppm (1H, s, ArOH diastereomer XIIa), $\delta = 12.52$ ppm (1H, s, ArOH, diastereomer XIIa), $\delta = 12.45$ ppm (1H, s, ArOH, diastereomer XIIb), $\delta = 12.43$ ppm (1H, s, ArOH, diastereomer XIIb), $\delta = 7.17$–$7.53$ ppm (7H, m, ArH diastereomers XIIa and XIIb), $\delta = 4.84$–$5.06$ ppm (3H, OH, H(1), Ph—CH—Me, diastereomers XIIa and XIIb), $\delta = 3.42$–$3.54$ ppm (1H, H$_4$(eq), diastereomers XIIa and XIIb), $\delta = 2.70$–$2.85$ ppm (1H, H$_4$(ax), diastereomers XIIa and XIIb), $\delta = 1.88$–$2.31$ ppm (2H, H$_2$(eq and ax), diastereomers XIIa and XIIb), $\delta = 1.50$ ppm (3H, d, CH$_3$, diastereomer XIIb), $\delta = 1.42$ ppm (3H, d, CH$_3$, diastereomer XIIa), $\delta = 0.10$ ppm (9H, s, CH$_3$)$_3$, diastereomers XIIa and XIIb).

The ration of the diastereomers can be determined from the $^1$H-NMR spectrum by integration of the ArOH protons $\delta = 12.67 + 12.52 : 12.44$ ppm and the CH$_3$ protons $\delta = 1.42 : 1.5$ ppm. When using the S-(—) alcohol as the starting material this ratio was 75:25.

What I claim is:

1. Compound of the formula

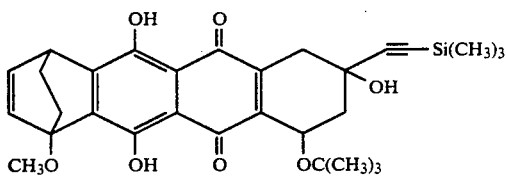

2. Compound of the formula

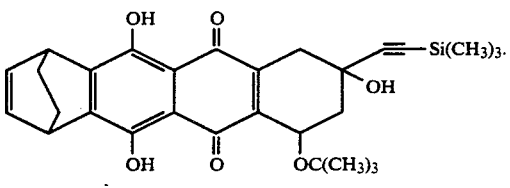

3. Compound of the formula

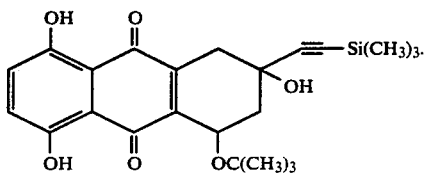

4. Compound of the formula

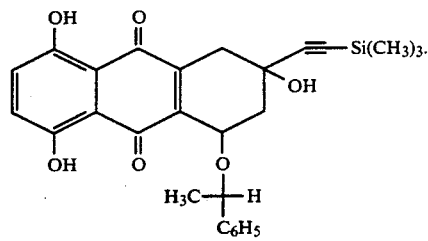

5. A compound of the formula:

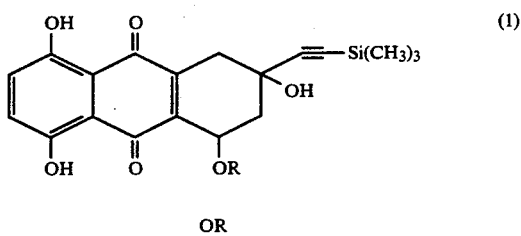

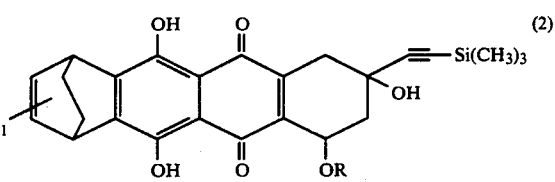

wherein R$_1$ is H, alkyl or alkoxy and R is a removable protecting group.

6. A process for preparing a compound in accordance with claim 9, consisting essentially of reacting a compound of the formula

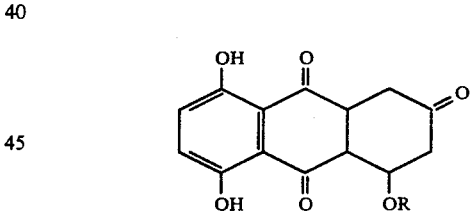

or a compound of the formula

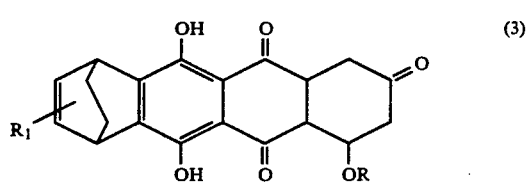

wherein R$_1$ and R have the meanings given in claim 1, with lithium trimethylsilyl acetylene and oxidizing the resultant reaction product.

7. A process according to claim 10 wherein said oxidizing is effected using lead tetraacetate.

8. A process for preparing daunomycinone or a derivative thereof having the formula

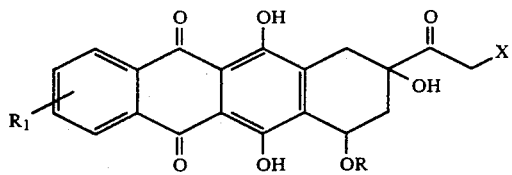

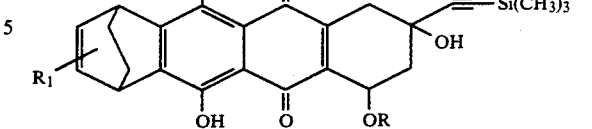

wherein X is H or OH, R is a removable protecting group and $R_1$ is H alkyl or alkoxy, comprising
providing a compound of the formula (1) or (2)

and
converting said compound (1) or (2) into daunomycinone or a derivative thereof.

9. A process according to claim 7 wherein said converting step comprises the following reaction scheme:

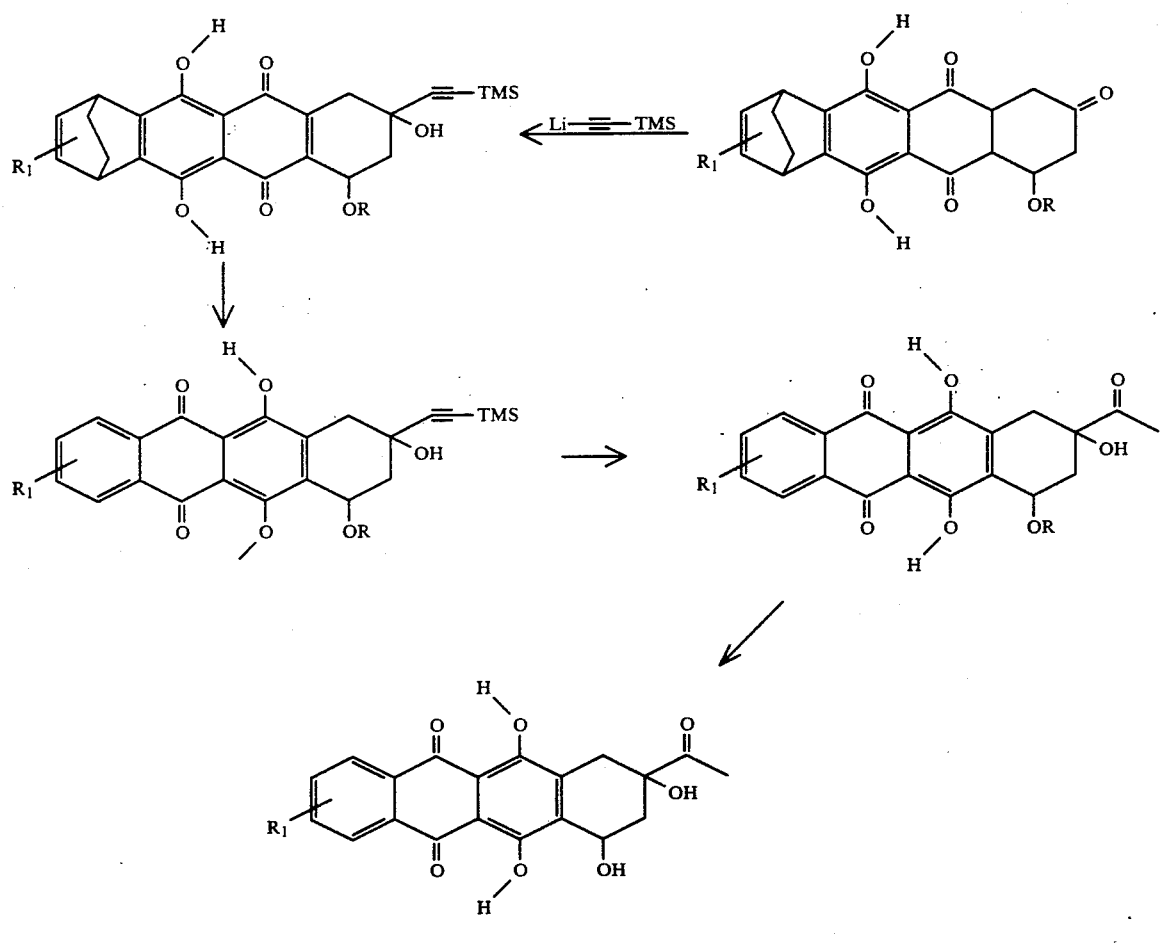

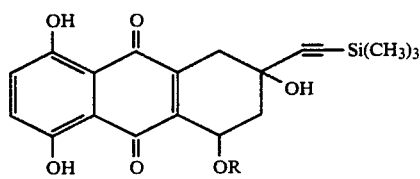

wherein TMS is trimethylsilyl.

10. A process according to claim 7 wherein said converting step comprises the following reaction scheme:

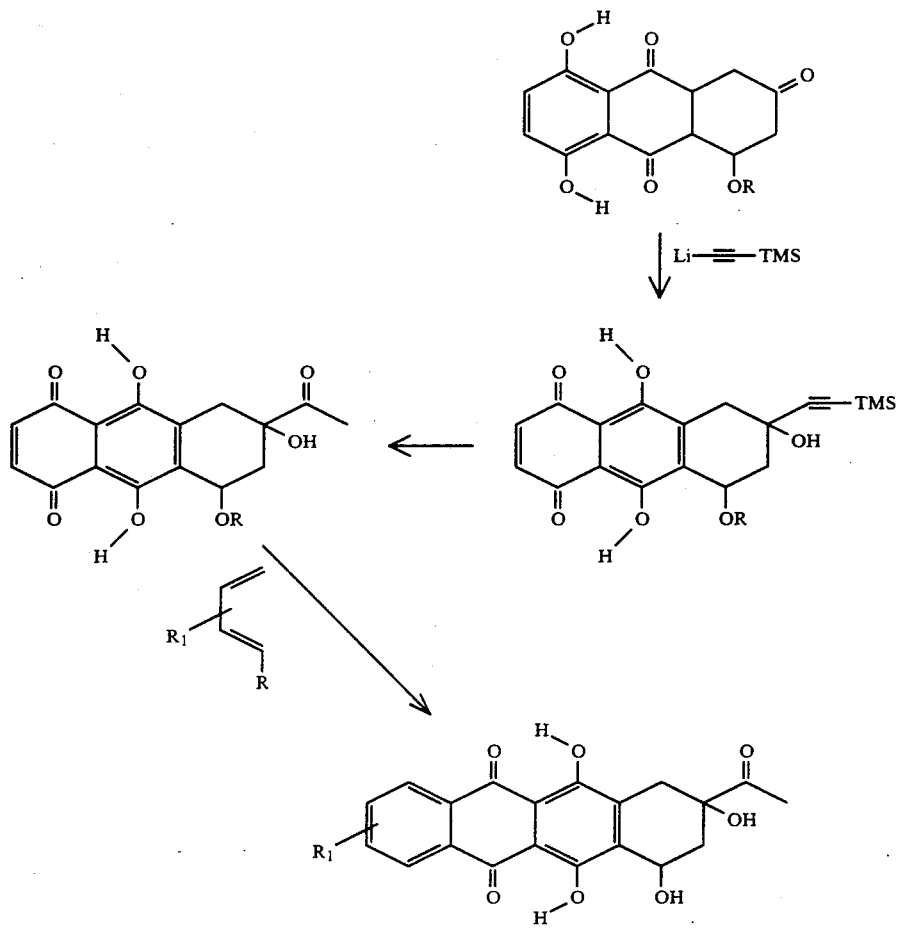
wherein TMS is trimethylsilyl.
* * * * *